United States Patent
Johnston, Jr.

(10) Patent No.: US 9,750,537 B2
(45) Date of Patent: Sep. 5, 2017

(54) CRANIAL DISTRACTOR

(75) Inventor: Thomas S. Johnston, Jr., Jacksonville, FL (US)

(73) Assignee: KLS-Martin, L.P., Jacksonville, FL (US)

( * ) Notice: Subject to any disclaimer, the term of this patent is extended or adjusted under 35 U.S.C. 154(b) by 916 days.

(21) Appl. No.: 13/440,261

(22) Filed: Apr. 5, 2012

(65) Prior Publication Data

US 2012/0259344 A1     Oct. 11, 2012

Related U.S. Application Data

(60) Provisional application No. 61/516,557, filed on Apr. 5, 2011.

(51) Int. Cl.
- A61B 17/58 (2006.01)
- A61B 17/60 (2006.01)
- A61F 2/00 (2006.01)
- A61B 17/66 (2006.01)
- A61B 17/80 (2006.01)

(52) U.S. Cl.
CPC .......... *A61B 17/66* (2013.01); *A61B 17/8004* (2013.01); *A61B 17/8061* (2013.01)

(58) Field of Classification Search
USPC .......... 606/105, 902–906, 57, 90, 282, 86 R, 606/86 B
See application file for complete search history.

(56) References Cited

U.S. PATENT DOCUMENTS

| | | | |
|---|---|---|---|
| 5,993,448 A * | 11/1999 | Remmler | 606/53 |
| 6,033,412 A | 3/2000 | Losken et al. | |
| 6,355,036 B1 * | 3/2002 | Nakajima | 606/57 |
| 7,621,922 B2 | 11/2009 | Schendel et al. | |
| 7,686,836 B2 | 3/2010 | Johnston et al. | |
| 7,704,251 B2 | 4/2010 | Huebner et al. | |
| 7,892,241 B2 | 2/2011 | Ahmad et al. | |
| 2005/0256526 A1 * | 11/2005 | Johnston | 606/69 |
| 2008/0039861 A1 * | 2/2008 | Ahmad et al. | 606/105 |
| 2012/0239035 A1 * | 9/2012 | Li | 606/57 |

FOREIGN PATENT DOCUMENTS

WO     2007117366 A2     10/2007

* cited by examiner

*Primary Examiner* — Si Ming Ku
(74) *Attorney, Agent, or Firm* — Thomas C. Saitta

(57) ABSTRACT

A pair of bone plates adapted for attachment to cranial bone segments, the cranial plates being mounted to a distraction mechanism such that the cranial plates can be separated gradually in very small increments. Each of the cranial plates is mounted to the distraction mechanism with a ball and socket connector assembly, such that each of the plates can move in multiple directions and orientations relative to the distraction mechanism to better accommodate a convex, planar or concave surface topography presented during the distraction procedure.

4 Claims, 2 Drawing Sheets

CRANIAL DISTRACTOR

This application claims the benefit of U.S. Provisional Patent Application Ser. No. 61/516,557, filed Apr. 5, 2011, the disclosure of which is incorporated herein by reference.

BACKGROUND OF THE INVENTION

This invention relates broadly to the field of medical devices known generally as bone distractors, which are devices designed to allow the distance between two bone segments to be gradually increased while bone regenerates in the area between the bone segments. In particular, the invention relates to cranial bone distractors, which are devices applied to two bone segments of the cranium. The distractors comprise in general a pair of bone plates mounted to a distraction assembly.

Bone regeneration or osteogenesis is a medical technique for repairing defective or damaged bones, such as for example when a bone fails to fully develop to its proper shape or size. An osteotomy or cut is made in the bone to produce two sides of exposed bone tissue and a distractor mechanism is attached to both bone segments. As new bone tissue is produced by the bone segments to bridge the gap, the distractor mechanism is used to gradually increase the distance between the bone segments. New bone tissue continues to be produced and eventually the proper shape or size for the bone is achieved. The distractor mechanism is then removed and the bone is allowed to heal and rigidify.

Bone distractors are well known in the art, but are primarily designed for linear distraction. Linear distraction is suitable for many bones, such as the mandible or the long bones of the legs or arms, but is not optimal for bones possessing curved topographical configurations, such as for example the cranium. A problem with known distractors when used with cranial distraction is that the linear distractors fail to accommodate the curvature of the cranium, such that the distraction does not result in formation of new bone having or approximating the appropriate curvature, instead producing a more planar area of new bone. It is an object of this invention to provide a cranial distractor that addresses this problem, wherein the distraction mechanism has a linear operation but the bone plates affixed to the opposing bone segments are mounted in a manner allowing free multi-directional movement to allow and account for the curvature and changes in the topography of the cranium during the osteogenesis process.

SUMMARY OF THE INVENTION

The invention comprises in general a pair of cranial bone plates adapted for attachment to cranial bone segments, the cranial plates being mounted to a linear distraction mechanism such that the cranial plates can be separated gradually in very small increments. Each of the cranial plates is mounted to the distraction mechanism with a ball and socket connector assembly, such that each of the plates can move in multiple directions and orientations relative to the distraction mechanism to account for the topographical changes of the cranium during osteogenesis such that the configuration of the regenerated bone better matches the desired final configuration of the cranium while simultaneously reducing stress on the cranial distractor. One cranial plate is mounted to the distraction mechanism in stationary position while the other cranial plate is mounted in a manner that allows for movement along the longitudinal axis of the distraction mechanism in the direction away from the other cranial plate.

DETAILED DESCRIPTION OF THE INVENTION

Figure 1:
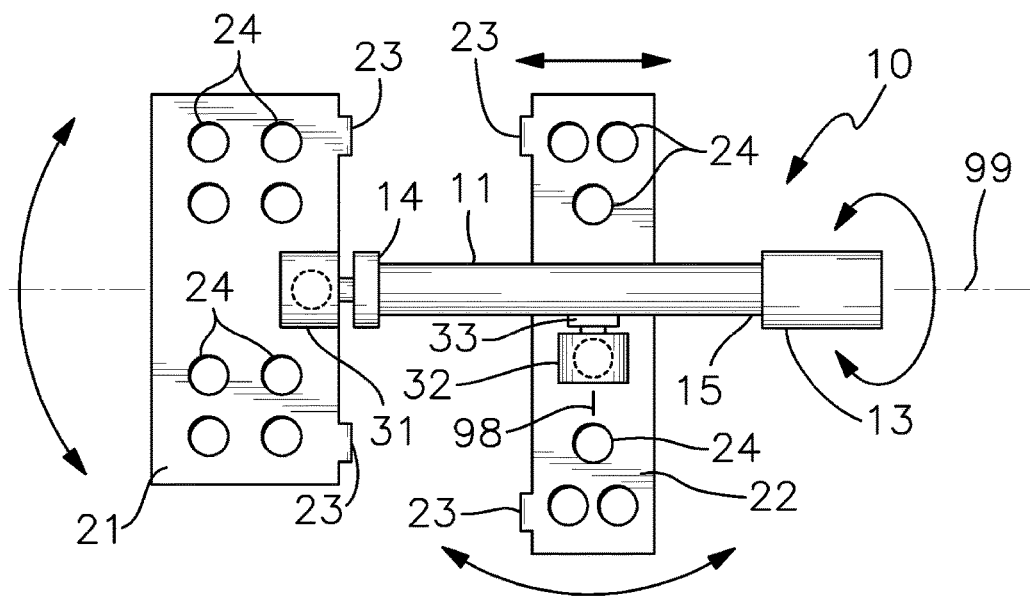
FIG. 1 is a top view of a representative embodiment of the cranial distractor, with arrows provided to illustrate the range of motion of various elements and structures.

With reference to the drawings, which are meant to be illustrative and not limiting, the invention will now be described in detail with regard for the best mode and the preferred embodiment. In general, the invention is a cranial distractor comprising two cranial bone plates structured for affixation to opposing cranial segments using mechanical fasteners, adhesive bonding or other suitable means, the bone plates being connected to a linear distraction mechanism defining a longitudinal axis whereby operation of the distraction mechanism increases the distance between the bone plates. Each of the bone plates is connected to the distraction mechanism by a ball and socket connector assembly such that each bone plate may tilt up and down, rotate about the axis defined by the ball and socket connector assembly, and swivel side to side. With this structure the cranial plates of the distractor will properly orient relative to whatever convex, planar or concave surface topology is presented by a particular area of the cranium during the distraction procedure.

The cranial distractor comprises a distal cranial bone plate member 21 and a proximal cranial bone plate member 22 connected or mounted to a linear distraction mechanism 10, the distraction mechanism 10 operating in known manner such that the distance between the distal cranial plate 21 and the proximal cranial plate 22 can be gradually increased. The distal and proximal cranial plates 21 and 22 are relatively thin in cross-section, and may be composed of a malleable material to allow the cranial plates 21 and 22 to be shaped to conform to the surface topography of the cranial segments to which they will be affixed. The cranial bone plates 21 and 22 are provided with bone screw receiving apertures 24 that allow the plates 21 and 22 to be affixed to opposing cranial bone segments in known manner using mechanical screw fasteners, either permanent or bioresorbable. The cranial bone plates 21 and 22 are sufficiently dimensioned in length and width so as to be readily attachable to the exterior of the cranial bone segments such that localized stresses are reduced. The cranial bone plates 21 and 22 are connected to the distraction mechanism 10 in a manner that allows for independent movement of each cranial plate 21 and 22 in multiple directions relative to the distraction mechanism 10. Depending abutment or tab members 24 may be provided which extend from the proximal side of the distal cranial plate 21 and from the distal side of the proximal cranial plate 22. These abutment members 24 abut against the sides or edges of the opposing cranial bone segments during the distraction process to further minimize local stresses.

Figure 2:
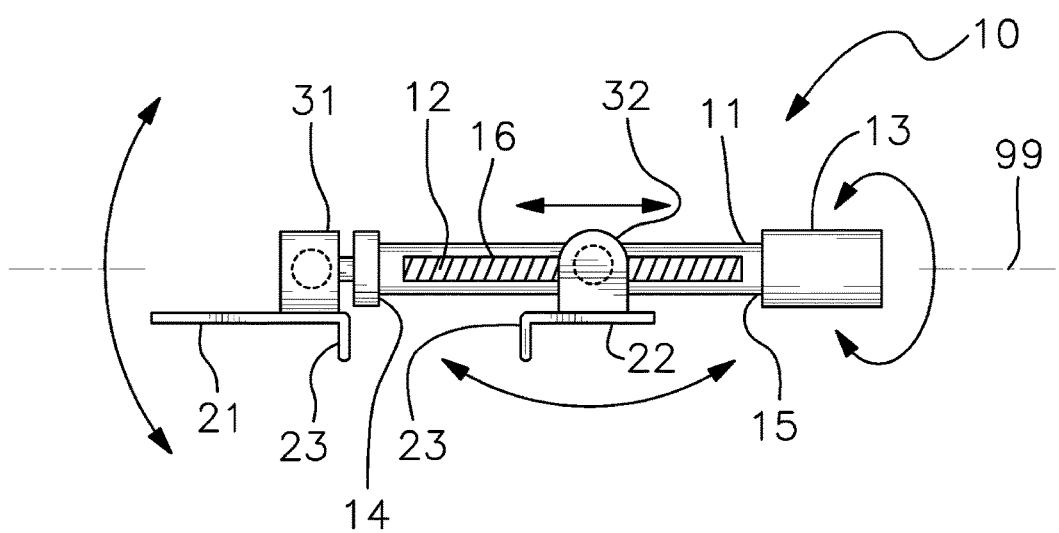
FIG. 2 is a side view of the embodiment of FIG. 1, with arrows provided to illustrate the range of motion of various elements and structures.
Figure 3:
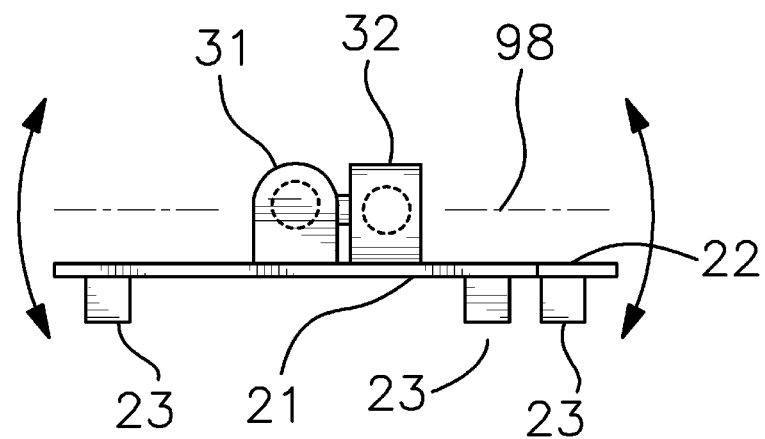
FIG. 3 is an end view of the embodiment of FIG. 1, with arrows provided to illustrate the range of motion of various elements and structures.

In the embodiment shown in FIGS. 1 through 3, the linear distraction mechanism 10 comprises a distal end 14, a proximal end 15 and an elongated sleeve member 11 defining a longitudinal axis 99 and provided with a longitudinal slot 16. A threaded drive rod 12 is received coaxially within the sleeve member 11 in a manner that allows for rotation of the drive rod 12 relative to the stationary sleeve member 11. A head member 13 attached to the proximal end of the drive rod 12 extends beyond the proximal end 15 of the sleeve member 11 and is used to rotate the drive rod 12, whether by finger manipulation or with the use of a drive tool.

The distal cranial plate 21 is joined to the distal end of the sleeve member 11 with a stationary ball and socket connector assembly 31, such that the stationary ball and socket assembly 31 does not move axially along the distraction mechanism 10. The ball and socket connector assembly 31 allows the distal cranial plate 21 to move in multiple directions relative to the axis 99 of the distraction mechanism 10, as shown by the arrows in the drawings. The distal cranial plate 21 may tilt up and down relative to the axis 99 of the distraction mechanism 10, swivel left and right relative to the axis 99 of the distraction mechanism 10, and rotate about the distraction mechanism axis 99, the axis defined by the ball and socket assembly 31 being coaxial to the distraction mechanism axis 99, such that the cranial plate 21 can be properly oriented for affixation to the cranial bone segment without creating detrimental stresses on the distraction mechanism 10 or the bone screws or other mechanical fasteners.

The proximal cranial plate 22 is joined to the drive rod 12 with a moving ball and socket connector assembly 32, and the moving ball and socket connector assembly 32 is connected to an internally threaded riding collar member 33 which is coaxially mounted onto the externally threaded drive rod and which extends through the slot 16 of the elongated sleeve member 11. As the drive rod 12 is rotated, the riding collar member 33 and the moving ball and socket connector assembly 32 moves longitudinally along the drive rod 12 in the axial direction. The moving ball and socket connector assembly defines a lateral or radial axis 98 extending outward to the distraction mechanism axis 99, and the moving ball and socket connector assembly 32 allows the proximal cranial plate 22 to move in multiple directions relative to the axis 98, as shown by the arrows in the drawings. The proximal cranial plate 22 may tilt up and down relative to the axis 98, swivel left and right relative to the axis 98, and rotate about the axis 98, such that the cranial plate 22 can be properly oriented for affixation to the other cranial bone segment without creating detrimental stresses on the distraction mechanism 10 or the bone screws or other mechanical fasteners. Furthermore, the cranial plates 21 and 22 are independently adjustable relative to each other.

With this structure, the cranial plates 21 and 22 are readily mountable to the cranial segments in proper conformation and are free to change orientation as they are gradually separated during the distraction procedure. This freedom accommodates the curvature of the cranium such that undesirable stresses are not imparted to the cranial bone segments and the configuration of the bone regeneration is able to approximate a natural curvature.

Figure 4:
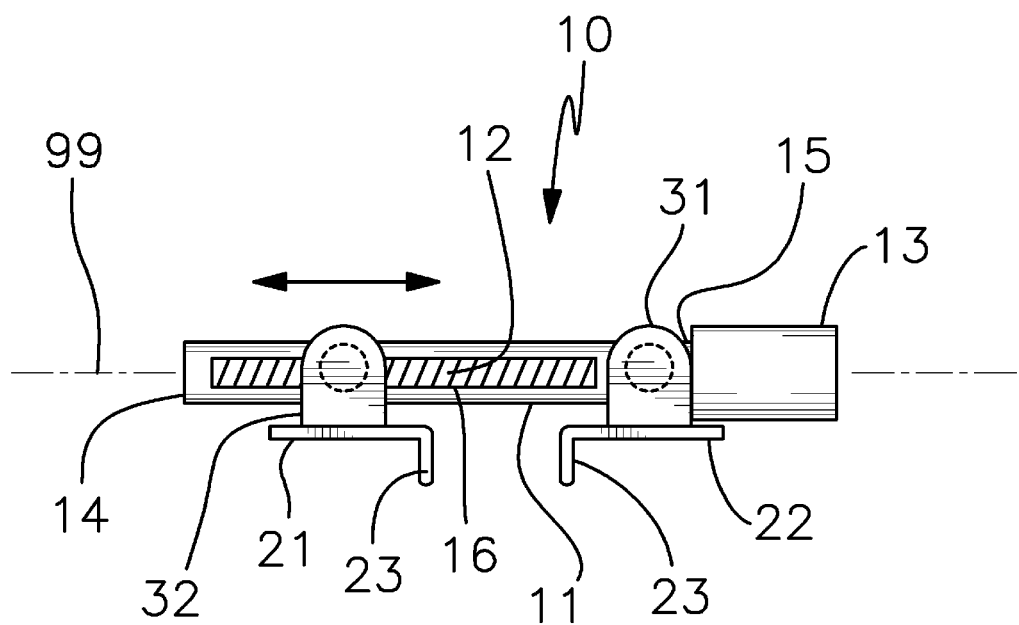
FIG. 4 is a side view of an alternative embodiment of the cranial distractor, wherein the distal cranial plate moves axially.

As shown in the alternative embodiment of FIG. 4, the affixation of the cranial plates 21 and 22 may be reversed such that the proximal cranial plate 22 is mounted by a fixed ball and socket connector assembly 31 to the proximal end 15 of the distraction mechanism and the distal cranial plate 21 is mounted by a moving ball and socket connector assembly 32 onto the internally threaded collar 33 positioned on the externally threaded drive rod 12, such that the distal cranial plate 21 moves longitudinally along the axis 99 away from the proximal cranial plate 22.

It is contemplated and understood that the cranial distractor may comprise distraction mechanisms having different operational mechanisms as long as the cranial plates are connected to the distractor assembly using ball and socket connector assemblies. Furthermore, while axial and lateral mountings for the ball and socket assemblies are preferred in order to minimize the overall height of the device such that the distractor mechanism remains close to the cranium, it is understood that the ball and socket assemblies could also be mounted beneath the distractor mechanism in an alternative embodiment, and the longitudinal slot could be disposed on the underside of the distractor mechanism.

It is to be understood that equivalents and substitutions to certain elements set forth above may be obvious to those ordinary skill in the art, and therefore the true scope and definition of the invention is to be as set forth in the following claims.

I claim:

1. A cranial distractor comprising:
    a linear distraction mechanism having a distal end, a proximal end and a longitudinal axis;
    a distal cranial plate affixed to said distraction mechanism by a ball and socket connector assembly;
    a proximal cranial plate affixed to said distraction mechanism by a ball and socket connector assembly;
    whereby operation of said distraction mechanism spreads apart said distal cranial plate and said proximal cranial plate;
    wherein said proximal cranial plate moves axially along said distraction mechanism;
    wherein said ball and socket connector assembly of said distal cranial plate is connected to said distal end of said distraction mechanism;
    wherein said ball and socket connector assembly of said distal cranial plate rotates about said longitudinal axis of said distraction mechanism.

2. A cranial distractor comprising:
    a linear distraction mechanism having a distal end, a proximal end and a longitudinal axis;
    a distal cranial plate affixed to said distraction mechanism by a ball and socket connector assembly;
    a proximal cranial plate affixed to said distraction mechanism by a ball and socket connector assembly;
    whereby operation of said distraction mechanism spreads apart said distal cranial plate and said proximal cranial plate;
    wherein said proximal cranial plate moves axially along said distraction mechanism;
    wherein said distraction mechanism comprises an externally threaded drive rod received within an elongated sleeve member having a longitudinal slot, and wherein said ball and socket connector assembly of said proximal cranial plate is connected to an internally threaded riding collar mounted on said externally threaded drive rod and extending through said longitudinal slot;
    wherein said ball and socket connector assembly of said distal cranial plate is connected to said distal end of said distraction mechanism;
    wherein said ball and socket connector assembly of said distal cranial plate rotates about said longitudinal axis of said distraction mechanism.

3. A cranial distractor comprising:
a linear distraction mechanism having a distal end, a proximal end and a longitudinal axis, said distraction mechanism comprising an externally threaded drive rod received within an elongated sleeve member having a longitudinal slot;
a distal cranial plate affixed to said distraction mechanism by a ball and socket connector assembly, whereby said distal cranial plate may tilt up and down, swivel left and right and rotate during a cranial distraction procedure;
a proximal cranial plate affixed to said distraction mechanism by a ball and socket connector assembly, whereby said proximal cranial plate may tilt up and down, swivel left and right and rotate during a cranial distraction procedure;
whereby rotation of said externally threaded drive rod relative to said elongated sleeve member of said distraction mechanism produces longitudinal movement of said distal cranial plate or said proximal cranial plate, thereby spreading apart said distal cranial plate and said proximal cranial plate;
wherein said ball and socket connector assembly of said distal cranial plate is connected to said distal end of said distraction mechanism;
wherein said ball and socket connector assembly of said distal cranial plate rotates about said longitudinal axis of said distraction mechanism.

4. A cranial distractor comprising:
a linear distraction mechanism having a distal end, a proximal end and a longitudinal axis, said distraction mechanism comprising an externally threaded drive rod received within an elongated sleeve member having a longitudinal slot;
a distal cranial plate affixed to said distraction mechanism by a ball and socket connector assembly, whereby said distal cranial plate may tilt up and down, swivel left and right and rotate during a cranial distraction procedure;
a proximal cranial plate affixed to said distraction mechanism by a ball and socket connector assembly, whereby said proximal cranial plate may tilt up and down, swivel left and right and rotate during a cranial distraction procedure;
whereby rotation of said externally threaded drive rod relative to said elongated sleeve member of said distraction mechanism produces longitudinal movement of said distal cranial plate or said proximal cranial plate, thereby spreading apart said distal cranial plate and said proximal cranial plate;
wherein said ball and socket connector assembly of said proximal cranial plate is connected to an internally threaded riding collar mounted on said externally threaded drive rod and extending through said longitudinal slot;
wherein said ball and socket connector assembly of said distal cranial plate is connected to said distal end of said distraction mechanism;
wherein said ball and socket connector assembly of said distal cranial plate rotates about said longitudinal axis of said distraction mechanism.

\* \* \* \* \*